US011660073B2

(12) United States Patent
Degertekin et al.

(10) Patent No.: US 11,660,073 B2
(45) Date of Patent: May 30, 2023

(54) FOLDABLE 2-D CMUT-ON-CMOS ARRAYS

(71) Applicants: GEORGIA TECH RESEARCH CORPORATION, Atlanta, GA (US); BIOSENSE WEBSTER (ISRAEL) LTD., Yokneam (IL)

(72) Inventors: F. Levent Degertekin, Atlanta, GA (US); Meir Bar-Tal, Yokneam (IL)

(73) Assignees: GEORGIA TECH RESEARCH CORPORATION, Atlanta, GA (US); BIOSENSE WEBSTER (ISRAEL) LTD., Yokneam (IL)

( * ) Notice: Subject to any disclaimer, the term of this patent is extended or adjusted under 35 U.S.C. 154(b) by 775 days.

(21) Appl. No.: 15/333,035

(22) Filed: Oct. 24, 2016

(65) Prior Publication Data
US 2017/0119348 A1      May 4, 2017

Related U.S. Application Data

(60) Provisional application No. 62/248,400, filed on Oct. 30, 2015.

(51) Int. Cl.
*A61B 8/00* (2006.01)
*G01S 15/89* (2006.01)
(Continued)

(52) U.S. Cl.
CPC .............. *A61B 8/4488* (2013.01); *A61B 8/12* (2013.01); *A61B 8/4254* (2013.01);
(Continued)

(58) Field of Classification Search
CPC ............. G01S 15/8934; G01S 15/8929; G01S 15/8925; G01S 15/8913; G01S 7/52079;
(Continued)

(56) References Cited

U.S. PATENT DOCUMENTS 5,569,197 A * 10/1996 Helmus ................. A61M 25/09
604/102.02
5,713,363 A * 2/1998 Seward .................... A61B 8/12
600/437
(Continued)

FOREIGN PATENT DOCUMENTS

AU      2016343928 A1      2/2013
CN      101868185 A       10/2010
(Continued)

OTHER PUBLICATIONS

Extended European Search Report for corresponding European patent application EP 16860572.3, dated Jun. 26, 2019.
(Continued)

*Primary Examiner* — Amelie R Davis
*Assistant Examiner* — Helene Bor
(74) *Attorney, Agent, or Firm* — Notaro, Michalos & Zaccaria P.C.

(57) ABSTRACT

Apparatus, including an insertion tube, configured to be inserted into a body cavity and having a first lumen having a first lumen diameter and a distal opening, and a tubular channel, having a second lumen and an outer channel diameter smaller than the first lumen diameter, inserted into the first lumen. The apparatus includes a support structure, configured to be passed through a space between an inner wall of the insertion tube and an outer wall of the tubular channel to the distal opening in a folded state and to unfold, upon exit of the support structure through the distal opening, in a direction transverse to the first lumen to reach a support dimension that is greater than the first lumen diameter. A plurality of planar two-dimensional arrays of ultrasonic transducers are supported by the support structure, the arrays having transverse dimensions less than the first lumen diameter.

4 Claims, 13 Drawing Sheets

(51) Int. Cl.
G01S 7/52 (2006.01)
A61B 8/12 (2006.01)
A61B 1/018 (2006.01)
A61B 1/00 (2006.01)

(52) U.S. Cl.
CPC .......... *A61B 8/4477* (2013.01); *A61B 8/4494* (2013.01); *G01S 7/52079* (2013.01); *G01S 15/8913* (2013.01); *G01S 15/8925* (2013.01); *G01S 15/8929* (2013.01); *G01S 15/8934* (2013.01); *A61B 1/0011* (2013.01); *A61B 1/018* (2013.01)

(58) Field of Classification Search
CPC ... A61B 8/4494; A61B 1/0011; A61B 8/4477; A61B 8/4254; A61B 1/018; A61B 8/12; A61B 8/4488; A61B 1/0008; A61B 1/00183; A61B 1/00096; A61B 1/051; A61B 1/05; A61B 8/0422; A61B 18/1492
See application file for complete search history.

(56) References Cited

U.S. PATENT DOCUMENTS

| | | | | |
|---|---|---|---|---|
| 5,846,196 A | * | 12/1998 | Siekmeyer | A61B 5/0422 600/374 |
| 5,976,345 A | * | 11/1999 | Pal | C25C 3/00 205/336 |
| 6,039,693 A | * | 3/2000 | Seward | A61B 8/06 128/916 |
| 6,099,475 A | * | 8/2000 | Seward | A61B 8/06 128/916 |
| 6,129,672 A | * | 10/2000 | Seward | A61B 8/06 128/916 |
| 6,162,175 A | * | 12/2000 | Marian, Jr. | A61B 8/12 600/447 |
| 6,171,247 B1 | * | 1/2001 | Seward | A61B 8/12 128/916 |
| 6,283,921 B1 | | 9/2001 | Nix et al. | |
| 6,306,096 B1 | * | 10/2001 | Seward | A61B 8/06 600/463 |
| 6,482,162 B1 | * | 11/2002 | Moore | A61B 8/12 600/459 |
| 6,494,843 B2 | * | 12/2002 | Edwardsen | A61B 5/6885 600/463 |
| 7,500,954 B2 | | 3/2009 | Wilser et al. | |
| 7,544,166 B2 | | 6/2009 | Yuan et al. | |
| 8,766,459 B2 | | 7/2014 | Degertekin et al. | |
| 8,891,334 B2 | | 11/2014 | Degertekin et al. | |
| 9,310,485 B2 | | 4/2016 | Degertekin et al. | |
| 10,820,887 B2 | * | 11/2020 | Bar-Tal | A61B 8/4488 |
| 2002/0002371 A1 | | 1/2002 | Acker et al. | |
| 2002/0026118 A1 | * | 2/2002 | Govari | A61B 5/062 600/462 |
| 2004/0242999 A1 | * | 12/2004 | Vitek | A61B 17/2202 600/437 |
| 2005/0215895 A1 | * | 9/2005 | Popp | A61B 8/4494 600/437 |
| 2006/0075818 A1 | * | 4/2006 | Huang | B06B 1/0292 73/649 |
| 2006/0276711 A1 | * | 12/2006 | Yuan | A61B 8/12 600/437 |
| 2007/0027445 A1 | | 2/2007 | Gifford et al. | |
| 2007/0066902 A1 | * | 3/2007 | Wilser | A61B 8/445 600/459 |
| 2007/0167752 A1 | * | 7/2007 | Proulx | G01S 7/52095 600/437 |
| 2008/0146937 A1 | * | 6/2008 | Lee | A61B 8/12 600/462 |
| 2010/0280388 A1 | | 11/2010 | Huang | |
| 2011/0166455 A1 | * | 7/2011 | Cully | A61B 8/4245 600/463 |
| 2013/0031980 A1 | * | 2/2013 | Sako | B06B 1/0292 73/606 |
| 2013/0171490 A1 | * | 7/2013 | Rothkopf | H01M 10/613 156/60 |
| 2015/0025357 A1 | * | 1/2015 | Adler | A61B 1/0008 600/407 |
| 2017/0119348 A1 | | 5/2017 | Degertekin et al. | |

FOREIGN PATENT DOCUMENTS

| | | |
|---|---|---|
| CN | 103037772 A | 4/2013 |
| CN | 108135646 A | 6/2018 |
| EP | 3367943 A1 | 9/2018 |
| WO | 2014/124231 A1 | 8/2014 |
| WO | 2015/048321 A1 | 4/2015 |
| WO | 2017074875 A1 | 5/2017 |

OTHER PUBLICATIONS

International Search Report and Written Opinion for corresponding PCT application No. PCT/US2016/058524, dated May 4, 2017.
International Preliminary Report on Patentability for corresponding PCT application No. PCT/US2016/058524, dated May 1, 2018.
Chinese Search Report for corresponding Chinese patent application No. 2016800571522, dated Mar. 19, 2020.
Canadian office action for corresponding Canadian application No. 2,994,309, dated Jan. 19, 2021.
Wikipedia, "French catheter scale", https://en.wikipedia.org/w/index.php title=French_catheter_scale&oldid=1103372077, retrieved Sep. 16, 2022.

* cited by examiner

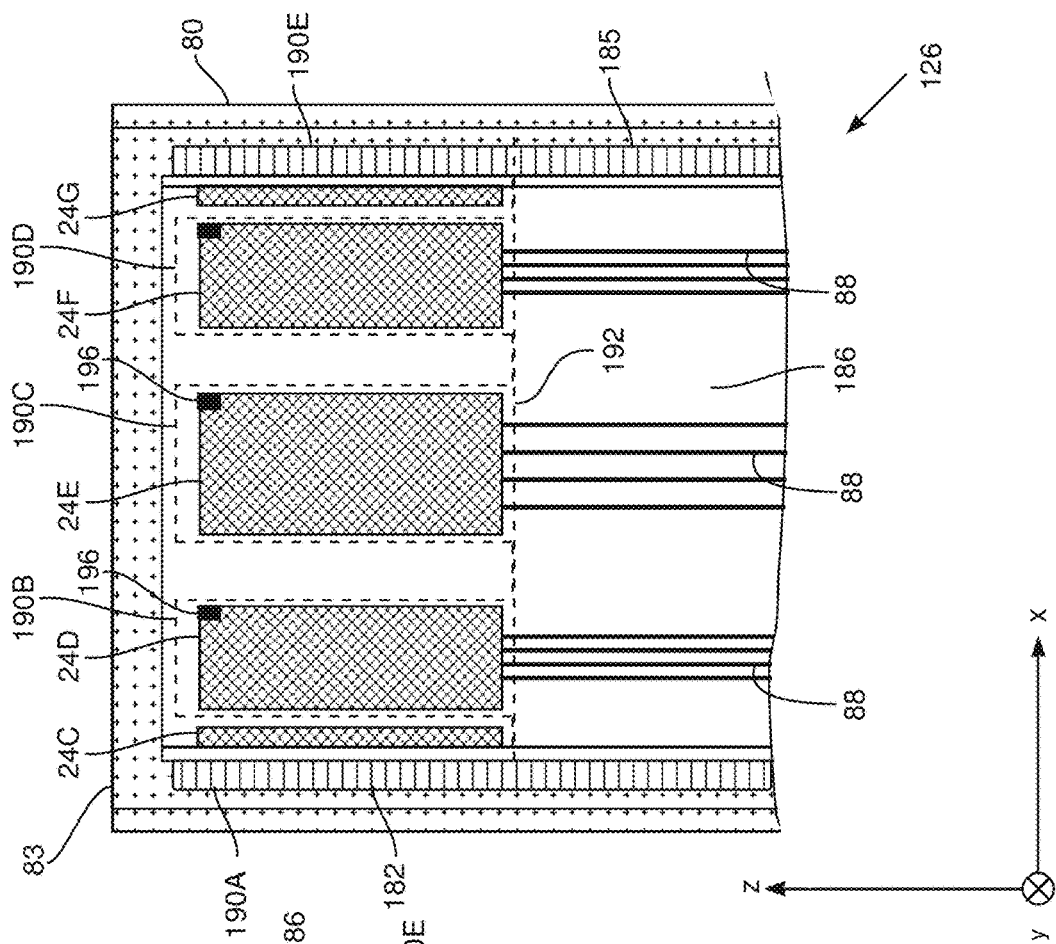
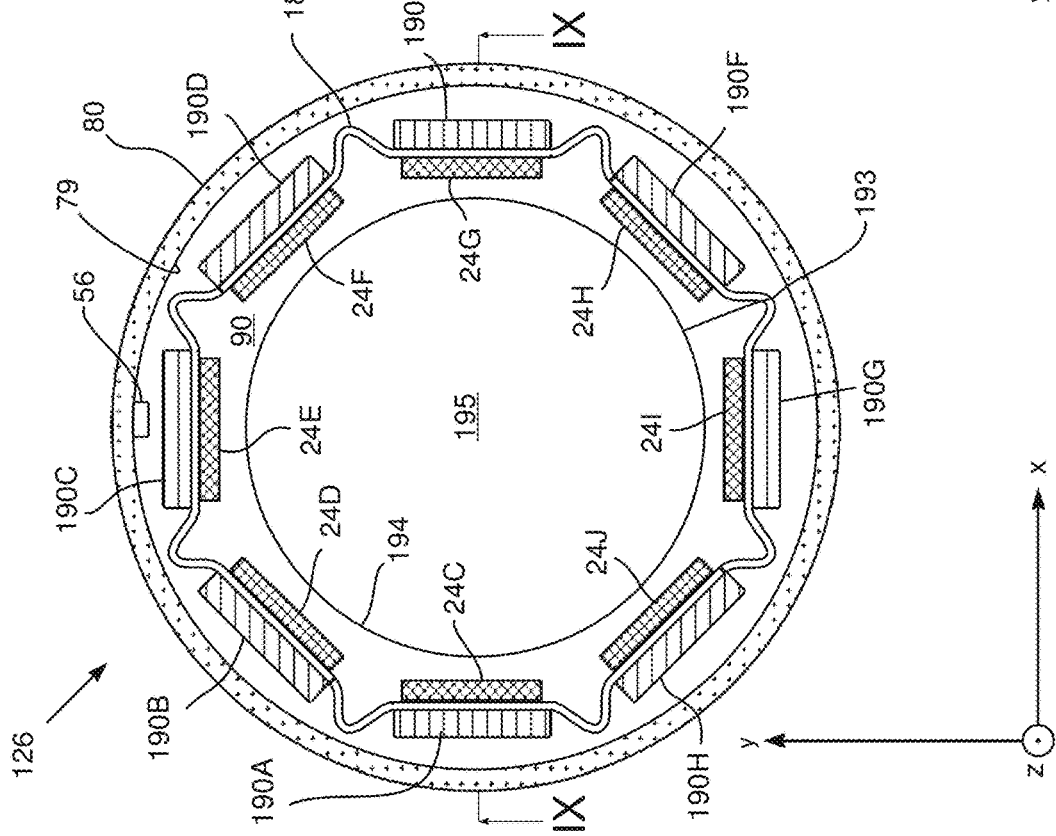

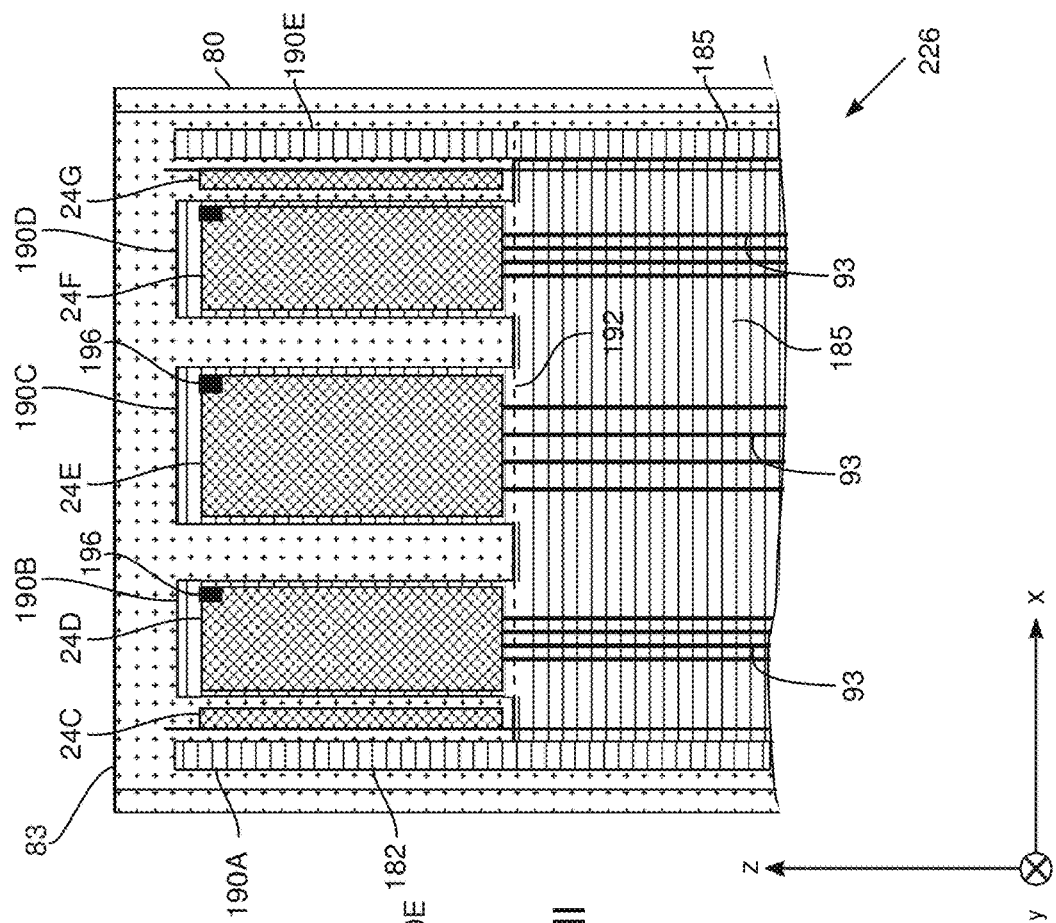
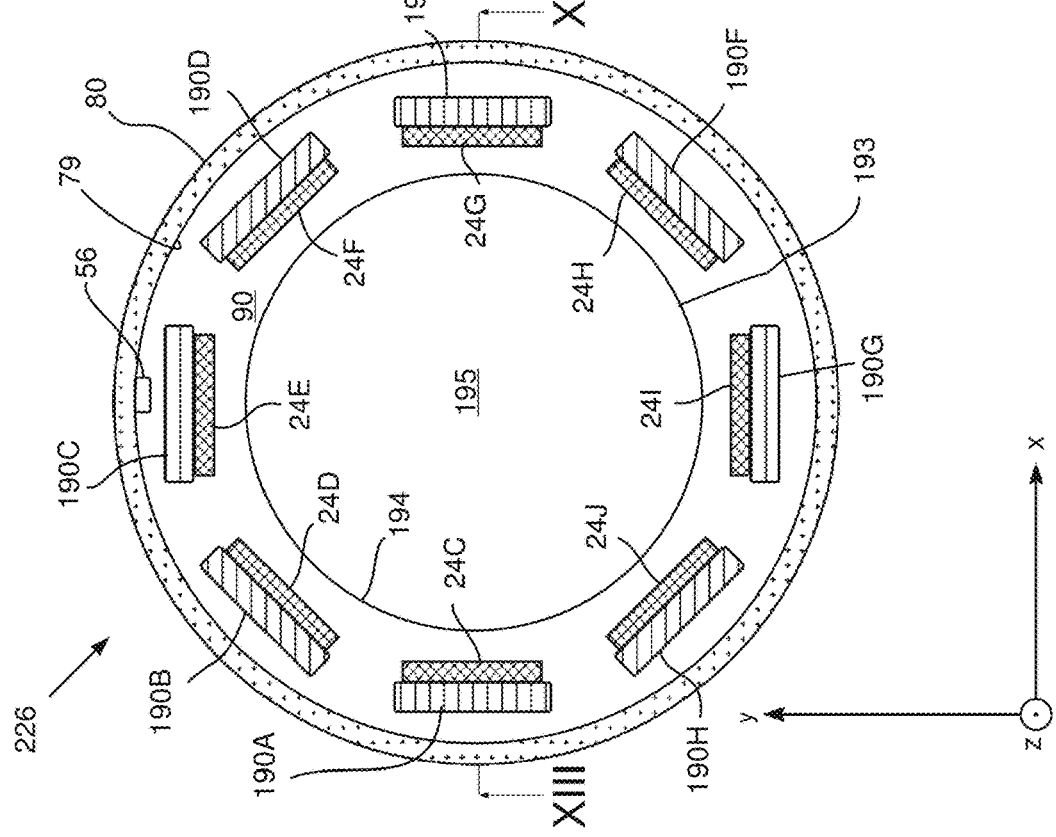
FIG. 13
FIG. 12

FOLDABLE 2-D CMUT-ON-CMOS ARRAYS

CROSS-REFERENCE TO RELATED APPLICATION

This application claims the benefit of U.S. Provisional Patent Application 62/248,400, filed Oct. 30, 2015, which is incorporated herein by reference.

FIELD OF THE INVENTION

The present invention relates generally to imaging, and specifically to ultrasound imaging using arrays of ultrasound transducers.

BACKGROUND OF THE INVENTION

Ultrasound transducer arrays are known in the art, and some examples of prior art describing such arrays are provided below.

U.S. Pat. No. 7,544,166 to Yuan, et al., whose disclosure is incorporated herein by reference, describes a medical device insertable into the body of a living being. The medical device has an imaging device with a layout that is adjustable from an undeployed layout, where the imaging device is insertable into the inner lumen of a medical device, to a larger deployed layout.

U.S. Pat. No. 7,500,954, and U. S. Patent Application 2007/0066902, to Wilser, et al., whose disclosures are incorporated herein by reference, describe a foldable transducer array that is unfolded or deployed for use, providing a larger radiating surface. While folded, the transducer array has a smaller width or volume for insertion into and withdrawal from a patient.

U.S. Pat. No. 8,766,459 to Degertekin, et al., whose disclosure is incorporated herein by reference, describes capacitive micromachined ultrasonic transducer ("CMUT") devices and methods for their fabrication. The CMUT devices can include integrated circuit devices utilizing direct connections to various CMOS (complementary metal oxide semiconductor) electronic components. The disclosure also states that CMUT devices can be manufactured on multiple silicon chip layers with each layer connected utilizing through silicon vias (TSVs).

U.S. Pat. No. 8,891,334 to Degertekin, et al., whose disclosure is incorporated herein by reference, describes a CMUT on a CMOS imaging chip. The imaging chip is stated to use direct connection and CMOS architecture to minimize both internal and external connection complexity. The disclosure also states that intelligent power management can enable the chip to be used for various imaging applications with strict power constraints, including forward-looking intra-vascular ultrasound imaging.

U.S. Pat. No. 9,310,485 to Degertekin, et al., whose disclosure is incorporated herein by reference, also describes a CMUT on a CMOS imaging chip. The CMOS architecture is stated to enable substantially the entire chip area to be utilized for element placement. The chip is also stated to be able to utilize arbitrarily selected transmit (Tx) and receive (Rx) element arrays to improve image quality, while reducing sampling time.

PCT Patent Application WO2015048321 to Degertekin, et al., whose disclosure is incorporated herein by reference, describes an intracardiac imaging system that has an intracardiac echography catheter. The catheter includes at least one CMUT on CMOS volumetric imaging chip disposed between a pair of coils. The catheter is stated to be made of MRI compatible materials and can include active cooling channels. The CMUT on CMOS chip is stated to have a plurality of Tx elements transmitting imaging pulses, a plurality of Rx elements disposed on the chip to have a large aperture, and a plurality of electronics interfacing with the Tx elements for beamforming, and with the Rx elements to produce radio frequency output signals.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus, including:

an insertion tube, configured to be inserted into a body cavity and having a first lumen therethrough having a first lumen diameter and a distal opening;

a tubular channel, having a second lumen therethrough and an outer channel diameter smaller than the first lumen diameter, inserted into the first lumen;

a support structure, which is configured to be passed through a space between an inner wall of the insertion tube and an outer wall of the tubular channel to the distal opening in a folded state and to unfold, upon exit of the support structure through the distal opening, in a direction transverse to the first lumen to reach a support dimension that is greater than the first lumen diameter; and a plurality of planar two-dimensional (2D) arrays of ultrasonic transducers supported by the support structure, the arrays having transverse dimensions less than the first lumen diameter.

The support structure may include two 2D supports connected by a hinge, and which fold about the hinge in countervailing directions to place the support structure in an unfolded state, and the plurality of planar 2D arrays may include two 2D arrays respectively mounted on the two 2D supports.

In an unfolded state of the support structure, the plurality of 2D arrays may lie in a single plane. A normal of the single plane may be orthogonal to a symmetry axis of the first lumen. Alternatively, the normal of the single plane may be parallel to the symmetry axis of the first lumen.

In a disclosed embodiment the apparatus includes at least one sensor fixedly positioned in proximity to at least one of the 2D arrays, the at least one sensor providing a location and an orientation of the at least one of the 2D arrays.

In a further disclosed embodiment the support structure includes two or more 2D separated supports connected to, and which fold about, a hinge in common directions to place the support structure in an unfolded state, and the plurality of planar 2D arrays includes two or more arrays respectively mounted on the two or more 2D separated supports.

The hinge may consist of a circular hinge. In some embodiments, in an unfolded state of the support structure, the circular hinge coincides with the distal opening.

The two or more 2D separated supports may be distributed symmetrically about a symmetry axis of the first lumen.

In a yet further disclosed embodiment the apparatus includes conductive wires connected directly to the 2D arrays as electrical interconnects thereof, so as to power the arrays and acquire signals therefrom.

In an alternative embodiment the apparatus includes a flexible substrate whereon the plurality of 2D arrays are mounted, the flexible substrate being mounted on the support structure. Typically, in an unfolded state of the support structure, the plurality of 2D arrays lie on a 2D disc formed by the substrate. The disc may have a central opening, and the central opening may have an opening diameter equal to the first lumen diameter.

In a further alternative embodiment the apparatus includes an ultrasound target fixedly positioned at a preset location with respect to the 2D arrays, and the 2D arrays are configured to acquire respective images of the target so as to register the arrays with respect to each other.

In a yet further alternative embodiment conductive traces are formed on the substrate and are connected to the 2D arrays as electrical interconnects thereof, so as to power the arrays and acquire signals therefrom.

The transducers may include capacitive micromachined ultrasonic transducers (CMUTs). Alternatively or additionally, the transducers may include piezoelectric micromachined ultrasonic transducers (pMUTs).

In an embodiment in the folded state the support structure completely surrounds the tubular channel.

In another embodiment in an unfolded state of the support structure, a proximal end of the support structure completely surrounds the tubular channel.

There is further provided, according to an embodiment of the present invention a method, including:

inserting an insertion tube into a body cavity, the tube having a first lumen therethrough having a first lumen diameter and a distal opening;

inserting a tubular channel, having a second lumen therethrough and an outer channel diameter smaller than the first lumen diameter, into the first lumen;

passing a support structure through a space between an inner wall of the insertion tube and an outer wall of the tubular channel to the distal opening in a folded state;

unfolding the support structure, upon exit of the support structure through the distal opening, in a direction transverse to the first lumen to reach a support dimension that is greater than the first lumen diameter; and supporting a plurality of planar two-dimensional (2D) arrays of ultrasonic transducers by the support structure, the arrays having transverse dimensions less than the first lumen diameter.

The present disclosure will be more fully understood from the following detailed description of the embodiments thereof, taken together with the drawings, in which:

BRIEF DESCRIPTION OF THE DRAWINGS

FIG. 8 and FIG. 9 illustrate an imaging array system in its folded state, according to a further alternative embodiment of the present invention; FIGS. 12, 13, 14, and 15 are schematic illustrations of the distal end of the probe, according to a yet further alternative embodiment of the present invention.

DETAILED DESCRIPTION OF EMBODIMENTS

Overview

Figure 1:
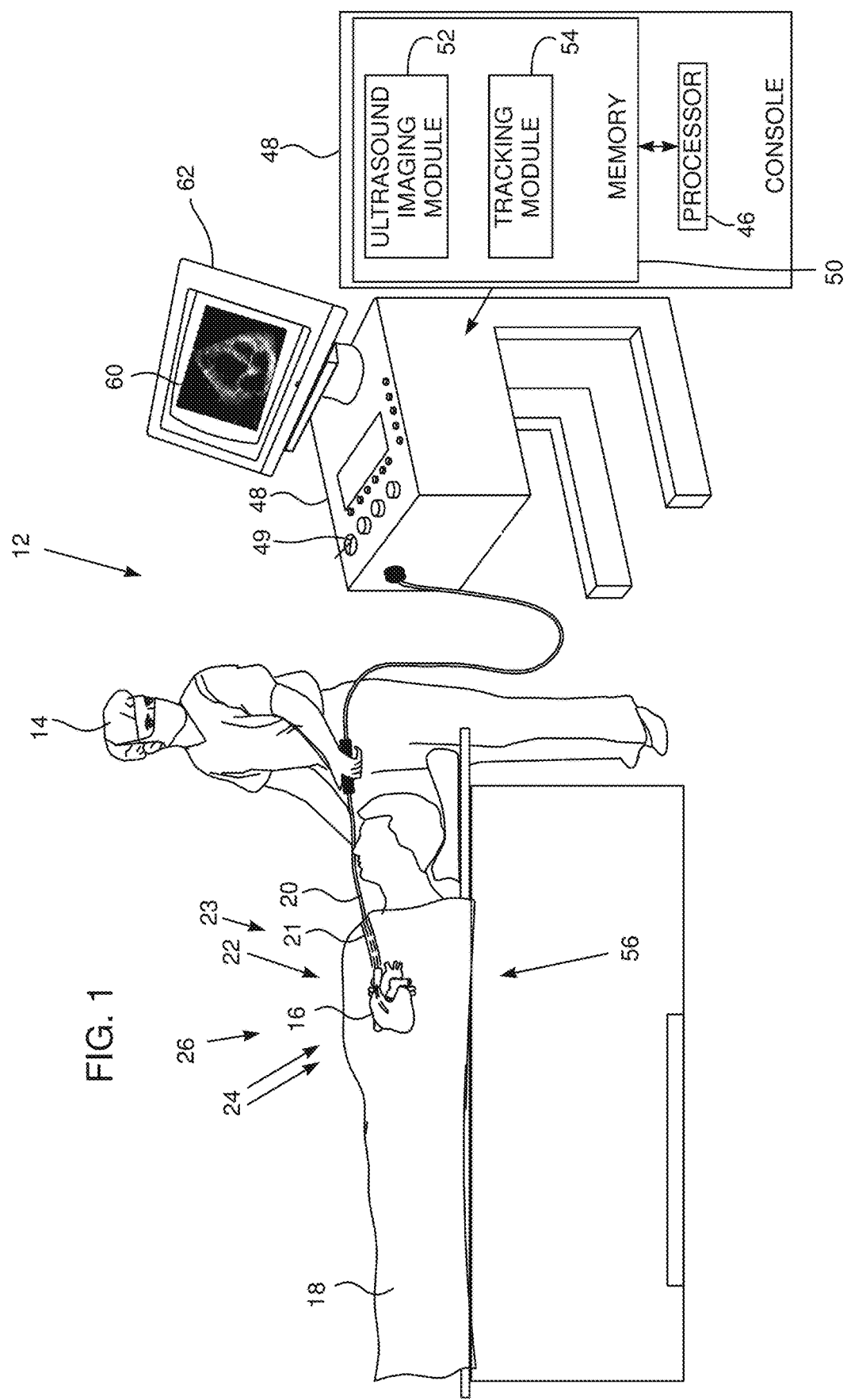
FIG. 1 is a schematic illustration of an invasive medical procedure using an imaging apparatus, according to an embodiment of the present invention.

Although there have been significant developments in both commercial and research phase intracardiac echography (ICE) systems, the resulting image quality is fundamentally limited by the physical size of the 7F-10F diameter ICE catheters. ICE catheters can be steered to provide favorable views of the anatomical features to guide interventions in the heart, but at their distal end they typically have 1-1.5 cm long rigid tips that carry one-dimensional (1D) or two-dimensional (2D) piezoelectric ultrasound imaging arrays. Since these piezoelectric transducer arrays are typically machined out of a single block of material and have backing structures with complex interconnects to connect each array element to the outside system separately, it is not feasible to provide a flexible tip. Consequently, the size of the 1D arrays in the elevation direction is limited to 2.3-3.3 mm whereas in the azimuth direction the arrays can be made as large as 10 mm. Thus, the 1D arrays provide good resolution in the azimuth direction but the resolution in the elevation direction is approximately three times worse. The size limitation also limits the total acoustic power that can be applied for imaging or therapeutic purposes.

In contrast, TEE (transesophageal echocardiogram) probes have a round shaped ~1 cm diameter 2D array aperture that can provide a balanced resolution in three-dimensional (3D) imaging space. However, TEE probes are limited in terms of frequency (3-5 MHz) and their size limits their access to the heart.

Therefore, there is a need for an approach to overcome the size limitations of the current ICE catheters to achieve good resolution 3D imaging in the heart. The present disclosure describes structures and methods to overcome these limitations using micromachined transducer arrays with integrated electronics that are placed over a structure containing electrical interconnects. The structure can be folded and unfolded. In its folded state the structure can fit into a narrow artery, and once the catheter reaches a desired location, such as inside a heart chamber, the catheter can then be unfolded and thus increase the effective imaging aperture.

In contrast with conventional piezoelectric transducer arrays, 2D capacitive micromachined ultrasonic transducers (CMUTs) can be fabricated on the same silicon chip with complex electronics to reduce the output electrical interconnect count. A similar approach can be used with piezoelectric micromachined ultrasonic transducers (pMUTs). This single chip system, or a stack of such chips, can be thinned down to 50-100 μm and may be placed on a flexible substrate upon which are printed electrical interconnect structures. Alternatively, the chip or chips may be placed directly on a foldable support structure, and the electrical interconnects may comprise conductive wires. Because of this flexibility, these structures can be folded to fit into a small space such as a narrow catheter, and the folded structures leave space in the catheter for other entities, as is described in more detail below.

Thus, in an embodiment of the present invention an insertion tube is configured to be inserted into a body cavity.

The tube encloses a first lumen having a first lumen diameter and a distal opening. A tubular channel, enclosing a second lumen and having an outer channel diameter smaller than the first lumen diameter, is inserted into the first lumen. A support structure is configured to be passed through a space between an inner wall of the insertion tube and an outer wall of the tubular channel to the distal opening in a folded state. The structure, upon exiting from the distal opening, unfolds in a direction transverse to the first lumen, and the unfolded structure has a support dimension that is greater than the first lumen diameter.

A plurality of planar two-dimensional (2D) arrays of ultrasonic transducers, typically CMUT or pMUT transducers, are supported by the support structure, the arrays having transverse dimensions less than the lumen diameter. In its folded state the embodiment fits into a narrow artery, whereas in an unfolded state, the arrays have a dimension greater than the lumen diameter. In addition, the tubular channel permits transfer of material to the distal opening regardless of whether the arrays are in a folded or unfolded state.

DETAILED DESCRIPTION

In the following description, like elements in the drawings are identified by like numerals, and the like elements are differentiated as necessary by appending a letter to the identifying numeral.

FIG. 1 is a schematic illustration of an invasive medical procedure using an imaging apparatus 12, according to an embodiment of the present invention. The procedure is performed by a medical professional 14, and, by way of example, the procedure in the description hereinbelow is assumed to comprise imaging of a portion of a myocardium 16 of the heart of a human patient 18. However, it will be understood that embodiments of the present invention are not just applicable to this specific procedure, and may include substantially any imaging of biological tissue or of non-biological material.

In order to perform the imaging, professional 14 inserts a probe 20 into a sheath 21 that has been pre-positioned in a lumen of the patient. Sheath 21 is positioned so that a distal end 22 of the probe may enter the heart of the patient, after exiting a termination 23 of the sheath. Distal end 22 incorporates a pair of generally similar two-dimensional (2D) ultrasound imaging arrays 24A, 24B comprised in an imaging array system 26. Details of probe 20, its distal end 22, arrays 24A, 24B also referred to herein as arrays 24, and array system 26 are provided below.

In one embodiment each transducer in any given array 24 is a capacitive micromachined ultrasonic transducer (CMUT). Typically each transducer in the CMUT array is directly connected to CMOS (complementary metal oxide semiconductor) components used to provide signals and power to, and receive signals from, the transducer. Examples of such transducers are described in U.S. Pat. Nos. 8,766,459, 8,891,334, and 9,310,485, referenced above. Other such transducers will be apparent to those having ordinary skill in the art, and all such transducers are assumed to be comprised within the scope of the present invention.

In another embodiment each transducer in any given array 24 is a piezoelectric micromachined ultrasonic transducer (pMUT).

As is known in the art, the transducers described above permit the use of a reduced number of electrical interconnects, typically approximately 30 such interconnects for each array 24A, 24B, for powering the transducers and for acquiring signals from the transducers. Embodiments of the present invention use this reduced number of electrical interconnects.

Using either CMUTs or pMUTs, a given array 24 may be formed as a single chip system, or as a stack of chips, which can be thinned down to 50-100 μm and placed on a flexible substrate which can contain electrical interconnect structures. This type of structure is described in the patents referenced above.

In one embodiment a given array 24 comprises a first 2D sub-array of ultrasound transducers configured as transmitters, and a second 2D sub-array of ultrasound transducers configured as receivers. The first and the second sub-arrays may have different geometric configurations, and examples of these configurations are provided in PCT Patent Application WO2015048321 referenced above. Other geometric configurations for the first and second sub-arrays will be apparent to those having ordinary skill in the ultrasound imaging arts, and all such configurations are assumed to be comprised within the scope of the present invention.

In an alternative embodiment any given 2D array 24 comprises ultrasound transducers that act as both transmitters and receivers.

In a further alternative embodiment any given 2D array 24 comprises a mixture of transducers, some of which are solely transmitters, some of which are solely receivers, and some of which act as both transmitters and receivers.

Apparatus 12 is controlled by a system processor 46, which is located in an operating console 48 of the apparatus. Console 48 comprises controls 49 which are used by professional 14 to communicate with the processor. During the procedure, processor 46 communicates with an ultrasound imaging module 52 in a memory 50, in order to generate images from ultrasound signals acquired by arrays 24 in array imaging system 26.

Module 52 enables the processor to provide driving voltages to the transducers on arrays 24. The module also enables the processor to receive signals generated by the transducers of arrays 24, and convert these signals into an image. It will be understood that the driving voltages to arrays 24, as well as the signals received from the arrays, depend upon whether the transducers of the arrays comprise CMUTs or pMUTs.

In order to operate apparatus 12, memory 50 typically comprises modules other than module 52, such as a tracking module 54 tracking the position and orientation of distal end 22. Module 54 uses a tracking sensor 56 located at the distal end of probe 20. By way of example, module 52 is assumed to comprise a magnetic tracking system, wherein the module controls magnetic fields that intersect sensor 56, and the module uses the signals consequently generated in the sensor to determine the location and position of the sensor, and thus of distal end 22. The Carto® system produced by Biosense Webster, of Diamond Bar, Calif., uses such a tracking module and associated sensor. Those having ordinary skill in the art will be aware of other types of tracking systems, and all such systems are included in the scope of the present invention.

Apparatus 12 may also use a force module for measuring the force on the distal end, and an irrigation module allowing the processor to control irrigation provided for the distal end. The Carto® system also uses such modules. Some of these modules, for example the force module, may require elements to be incorporated into the distal end. For simplicity, such elements are not referred to further in the present application, and such other modules are not illustrated in FIG. 1. All modules, including modules 52 and 54, may comprise hardware as well as software elements.

The software for processor 46 and memory 50 may be downloaded to the processor in electronic form, over a network, for example. Alternatively or additionally, the software may be provided on non-transitory tangible media, such as optical, magnetic, or electronic storage media.

Processor 46 uses module 52, and the signals acquired by arrays 24, to generate a 3D image 60 of myocardium 16. The processor presents the image on a screen 62.

Figure 2:
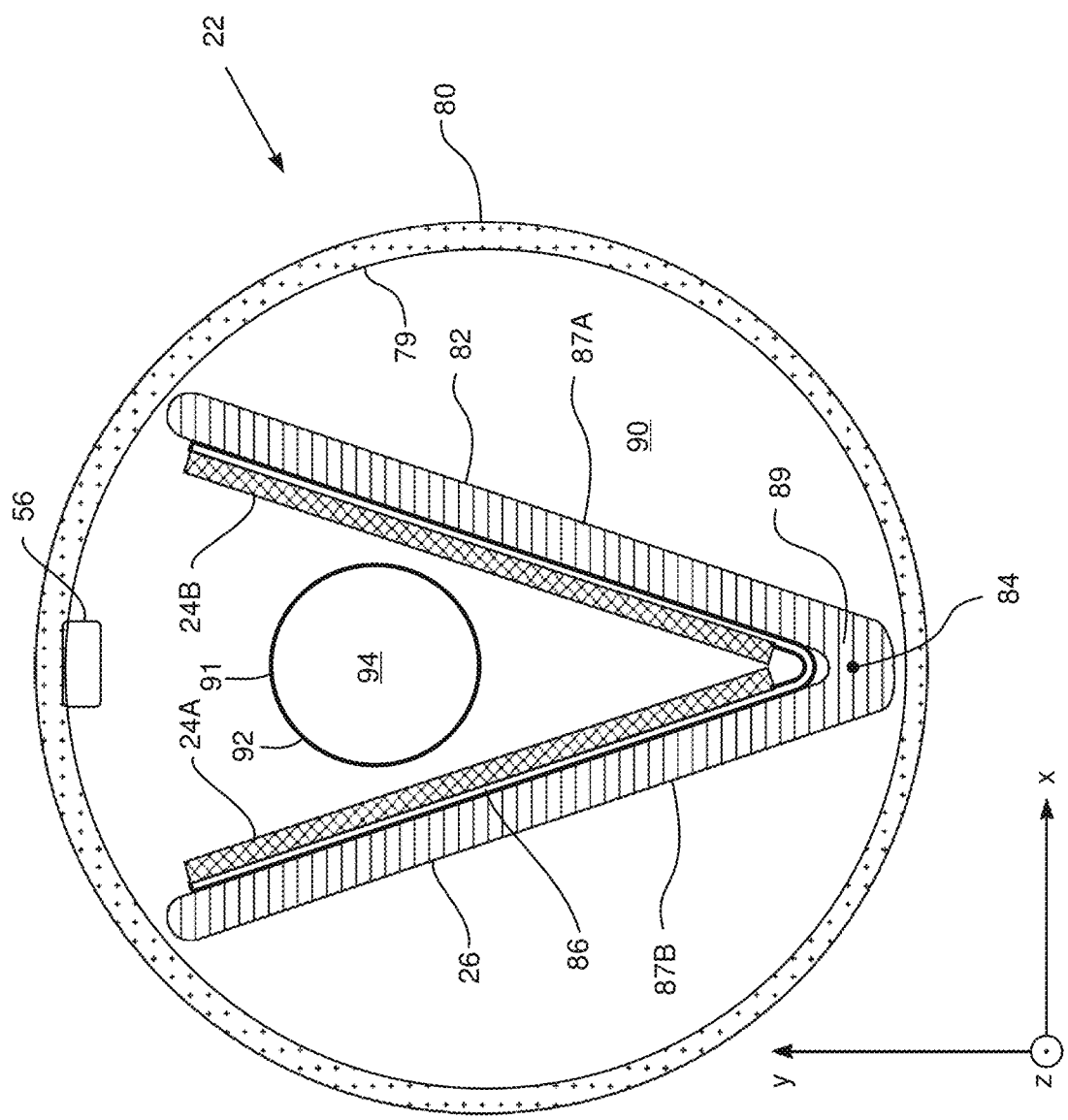
FIG. 2 and FIG. 3 are schematic illustrations of a distal end of a probe used in the imaging apparatus, according to an embodiment of the present invention.
Figure 3:
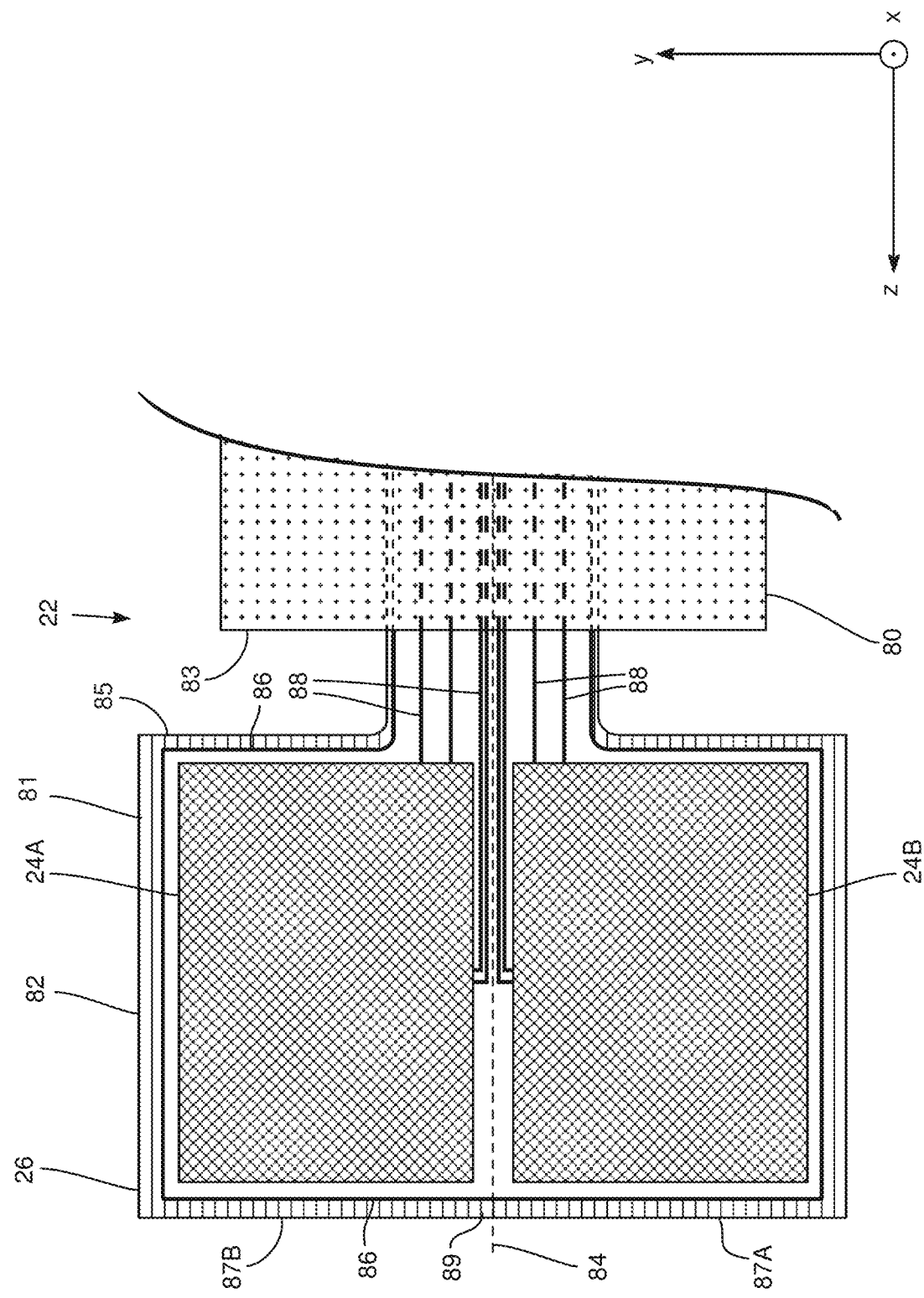

FIG. 2 and FIG. 3 are schematic illustrations of distal end 22 of probe 20, according to an embodiment of the present invention. Probe distal end 22 is assumed to be cylindrical, and for clarity has been drawn on a set of xyz orthogonal axes, where a central symmetry axis of the distal end is parallel to the z axis, which in FIG. 2 extends out of the page. FIG. 2 illustrates the probe distal end as it is being looked into, and shows probe distal end 22 as comprising an external insertion tube 80 enclosing a catheter lumen 90 having a lumen diameter. A tubular channel 92, having a diameter smaller than the lumen diameter, is positioned in lumen 90, the tubular channel enclosing a channel lumen 94. In one embodiment insertion tube 80 has dimensions between 7F and 10F.

FIG. 2 illustrates imaging array system 26 in its folded state, in which state the array system is able to fit completely within insertion tube 80, i.e. into lumen 90. As is illustrated in FIG. 2, system 26 in its folded state fits into a portion of lumen 90 lying between an inner wall 79 of tube 80 and an outer wall 91 of channel 92. FIG. 3 illustrates imaging array system 26 in its unfolded state, when a distal end 81 of system 26 has exited from a distal opening 83 of insertion tube 80.

System 26 is formed on a support structure 85, which has a distal end 82 of the structure that is foldable. Methods for implementing the folding and unfolding of structure 85 are described below. Typically, a proximal end of structure 85 does not fold. As is illustrated in the figures, imaging array system 26 comprises two substantially similar planar 2D arrays 24A, 24B which are mounted on a flexible circuit substrate 86, typically a flexible printed circuit substrate. Arrays 24A, 24B have transverse dimensions that are less than the diameter of lumen 90. Substrate 86 is in turn mounted on, and supported by, foldable structure distal end 82. Structure distal end 82 comprises two 2D generally rectangular supports 87A, 87B which are connected by a common element 89 that acts as a hinge, so that the two 2D supports fold about a hinge line 84, parallel to the z-axis, in element 87.

Electrical interconnects 88 from arrays 24A, 24B are formed on flexible printed circuit substrate 86, typically by lithographing conductive traces onto the substrate, the connections connecting the arrays to module 52 in console 48. As is described above, because of the structure of the transducers in arrays 24A, 24B, the number of interconnects 88 is reduced, typically to approximately 30.

In its folded state, because the transverse array dimensions are smaller than the lumen diameter, FIG. 2 illustrates that system 26 has a small enough profile to enable the system, while within insertion tube 80, to be threaded into a target site of interest, for example a chamber of the heart, through an artery for regular ICE imaging or transcatheter access, or through a hole in the heart for transapical access for valve implantation.

Once at the site of interest, in the chamber of the heart in this example, imaging array system 26 can be unfolded to its unfolded state, as shown in FIG. 3. The unfolding occurs by the system unfolding in a direction transverse to lumen 90, the two arrays rotating in countervailing directions about hinge line 84. To return to the folded state, the two arrays rotate in countervailing directions, opposite to those for the unfolding operation.

In the unfolded state of system 26 arrays 24A, 24B lie in a single yz plane that has a normal orthogonal to a symmetry axis of lumen 90. Arrays 24A, 24B form a support dimension that is substantially larger than the internal dimension of insertion tube 80, i.e., that is greater than the diameter of lumen 90. If insertion tube 80 has dimensions of 7F-10F, as stated above, then the internal dimension of the insertion tube, corresponding to the diameter, is approximately 3 mm. In one embodiment array system 26 in its unfolded state forms a rectangular 2D area having dimensions of 6 mm×6 mm.

FIG. 3 illustrates array system 26 operating as a "side-looking" imaging system, the system acquiring images in a direction orthogonal to the z-axis, i.e., orthogonal to the axis of the distal end. By way, of example, FIG. 3 illustrates system 26 when it is able to acquire images from a direction parallel to the x-axis.

Figure 4:
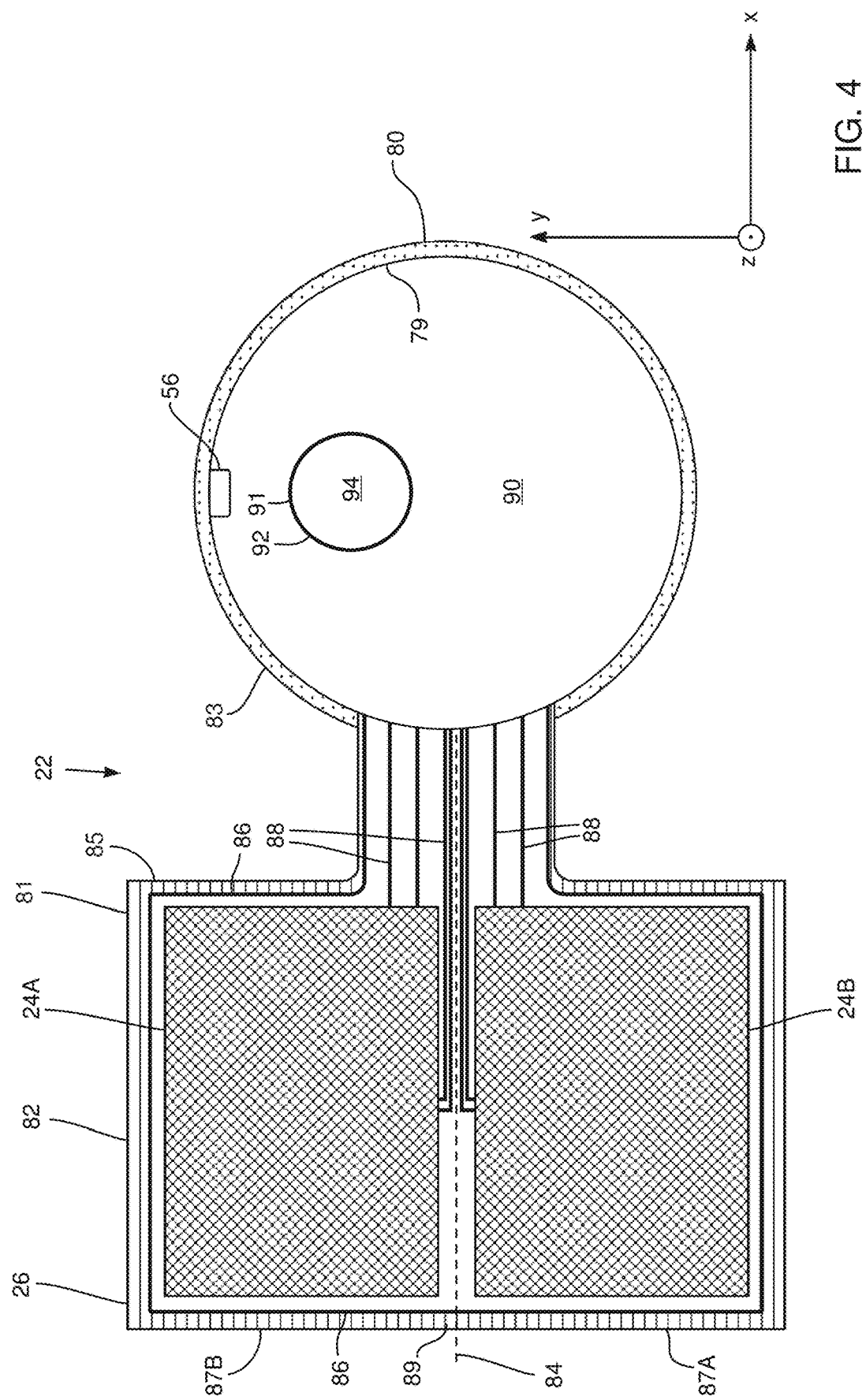
FIG. 4 is a schematic illustration of an imaging system when it is configured as a forward-looking imaging system, according to an embodiment of the present invention.

FIG. 4 is a schematic illustration of system 26 when it is configured as a forward-looking imaging system, according to an embodiment of the present invention. In the illustrated configuration, distal end 82 of system 26 has been further folded, from the configuration shown in FIG. 3, by 90° about opening 83 of insertion tube 80. Once the further folding has completed, arrays 24A, 24B lie in an xy plane, having a normal parallel to the lumen symmetry axis, and system 26 is able to acquire images from a direction parallel to the z-axis, i.e., parallel to the axis of the probe distal end.

Referring to FIGS. 1-4, it will be understood that system 26, in either its unfolded state (FIG. 3) or its further unfolded state (FIG. 4), can be returned to a folded state by reversing the unfolding operations. The folding and unfolding operations used by embodiments of the present invention may be implemented by one or more methods which are well known in the art. For example, the embodiments may incorporate mechanical control elements such as wires which can be operated by professional 14 to achieve both the folding and the unfolding operations, and the folding may be implemented about one or more hinge sections formed in structure 85. Alternatively or additionally, structure 85 may be constructed from a shape memory alloy such as nitinol, configured to locally fold about desired lines of the structure. Typically in this case the unfolding is achieved by structure distal end 82 no longer contacting insertion tube 80, and the folding by the structure distal end being withdrawn into the insertion tube.

It will be appreciated from inspection of FIGS. 2, 3, and 4, that material may be transferred to the distal opening of tube 80 via lumen 94, regardless of whether system 26 is in its folded or unfolded state. For example, irrigation fluid may be transferred via the lumen, and/or an ablation catheter may also be transferred and operated via the lumen. Other entities that will be familiar to those having skill in the art may also be transferred, and all such entities are included in the scope of the present invention.

Figure 5:
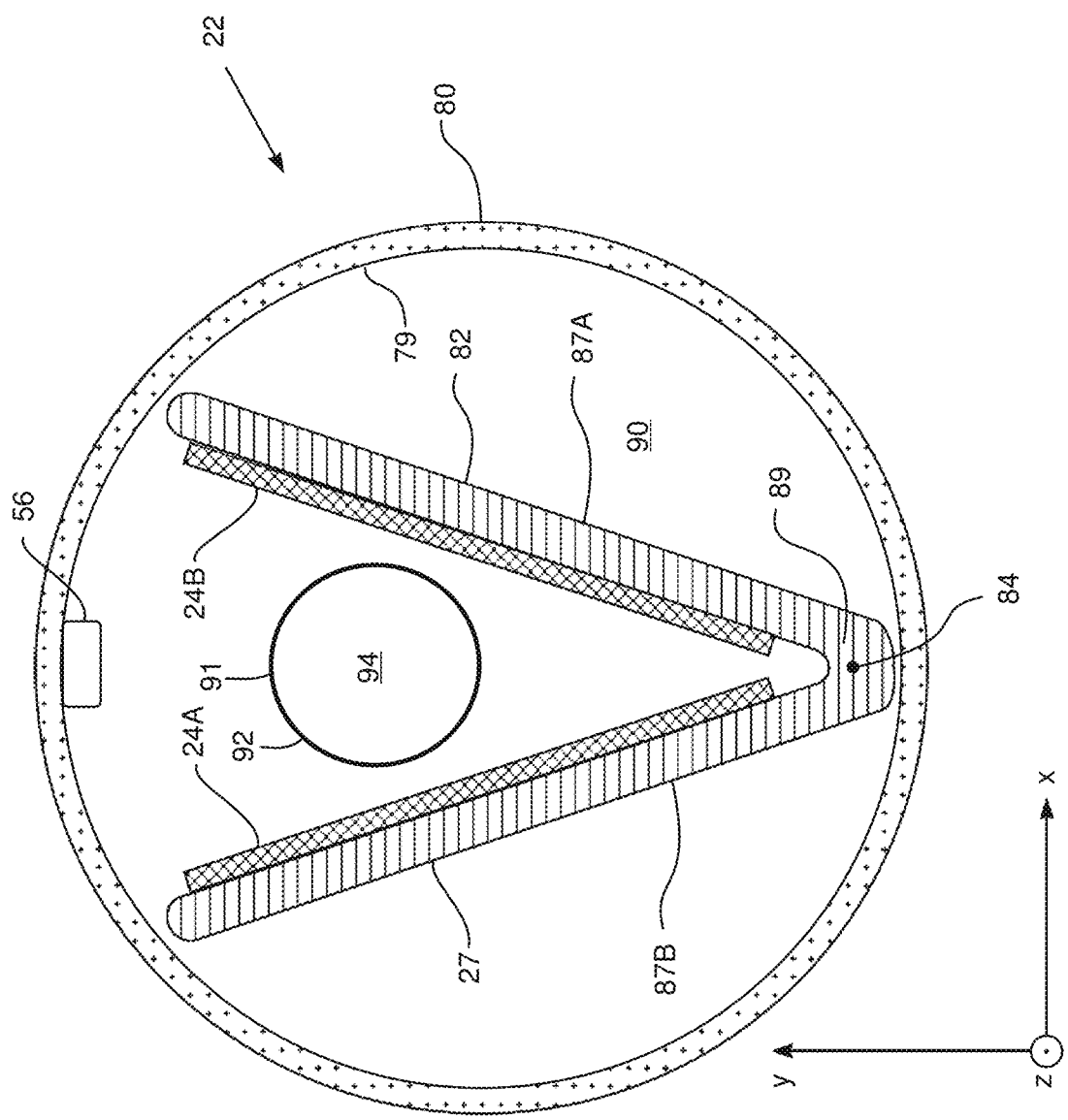
FIGS. 5, 6, and 7, are schematic illustrations of a distal end of a probe, according to an alternative embodiment of the present invention.
Figure 6:
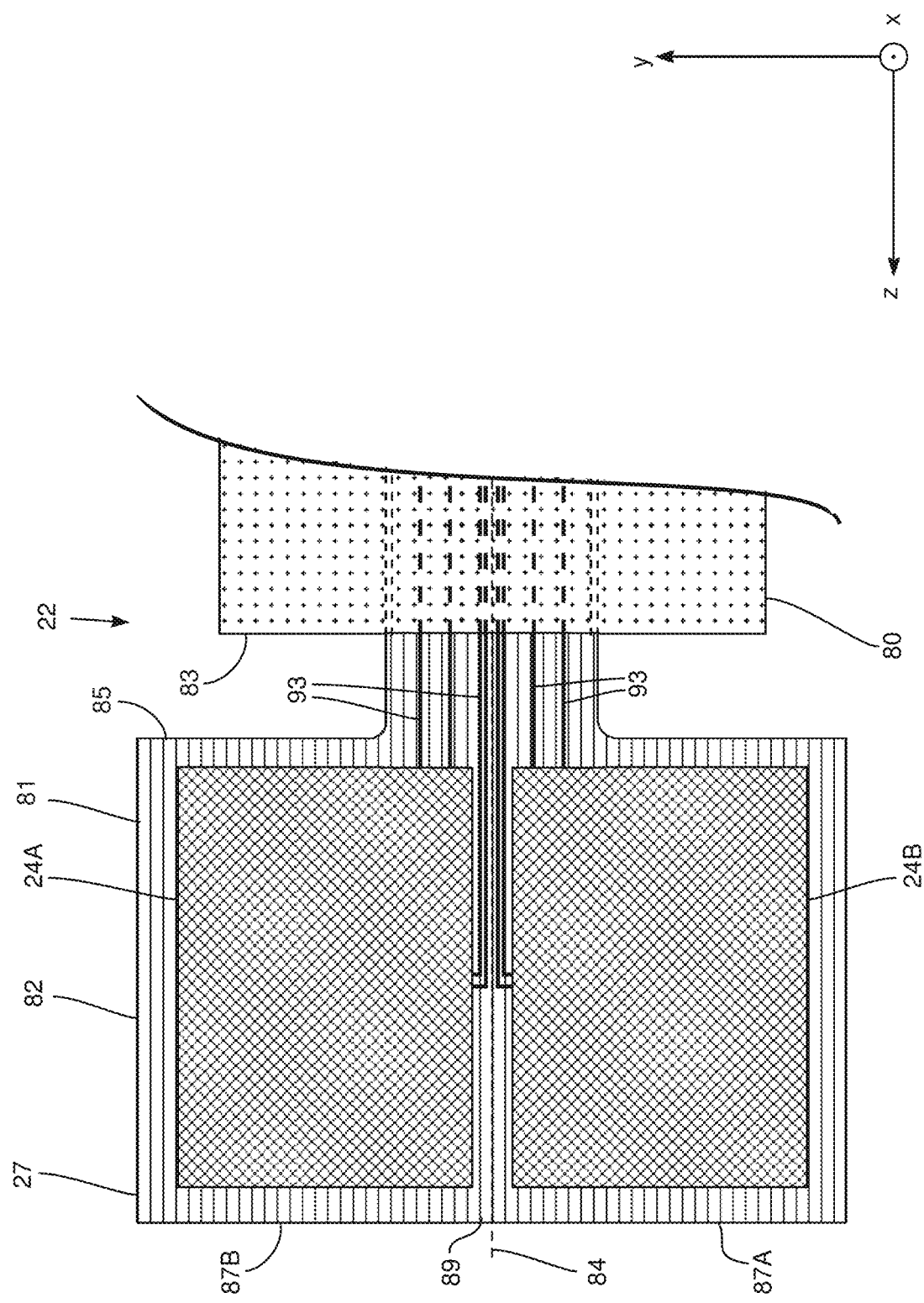
Figure 7:
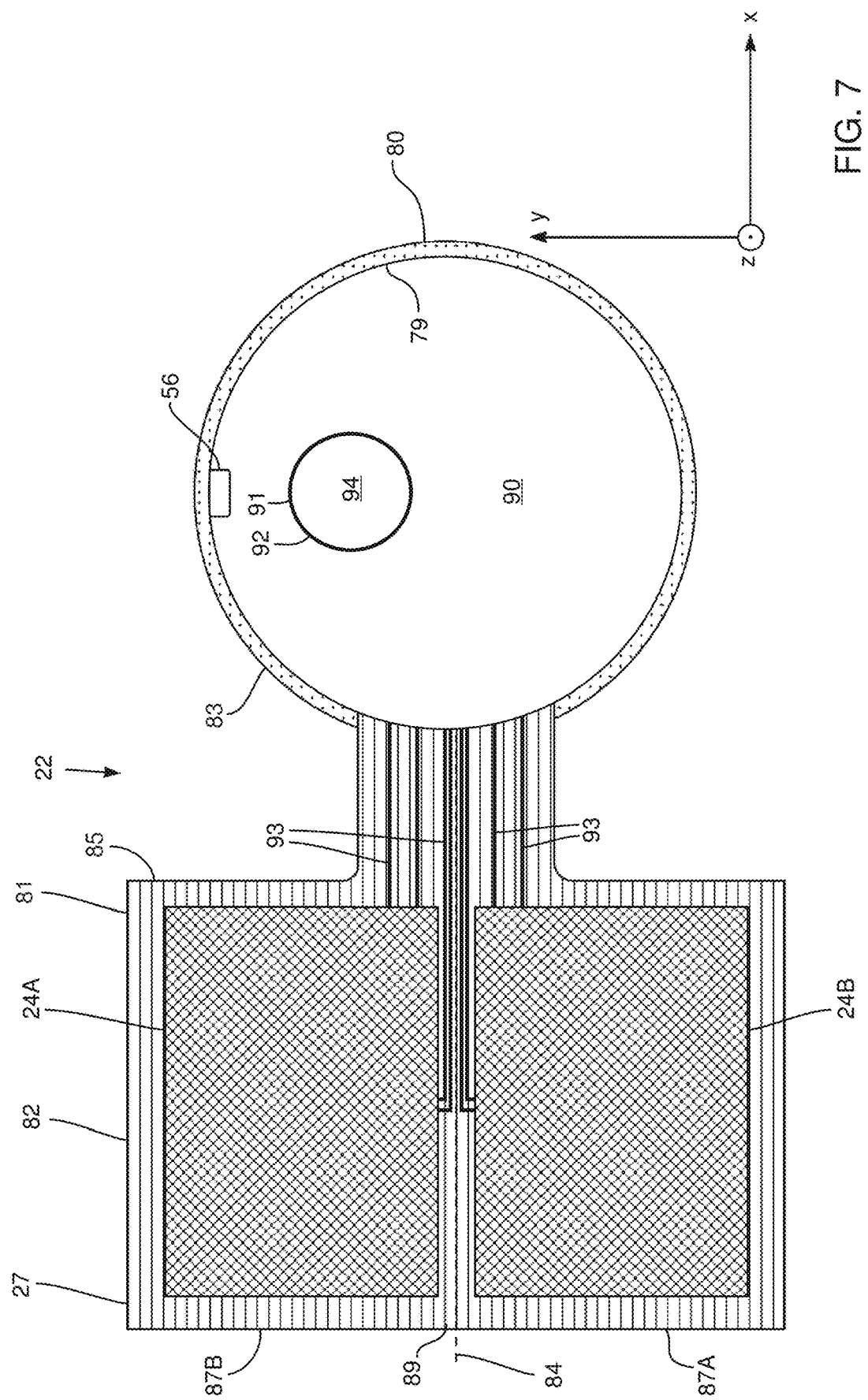

FIGS. 5, 6, and 7, are schematic illustrations of distal end 22 of probe 20, according to an alternative embodiment of the present invention. An imaging array system 27 is incorporated into probe distal end 22, and apart from the differences described below, the operation of system 27 is generally similar to that of system 26 (FIGS. 1-4), and the descriptions for FIGS. 2, 3, and 4 respectively apply, mutatis mutandis, to FIGS. 5, 6, and 7. Elements indicated by the same reference numerals in both systems 26 and 27 are generally similar in construction and in operation.

In contrast to system 26, system 27 does not use a flexible substrate 86. Rather, arrays 24A, 24B are respectively directly mounted on rectangular supports 87A, 87B. In addition, since there is no flexible substrate, electrical interconnects to the arrays are formed as conductive wires 93 that connect directly to the arrays.

FIGS. 8, 9, 10, and 11 are schematic illustrations of distal end 22 of probe 20, according to a further alternative embodiment of the present invention.

An imaging array system 126 is incorporated into probe distal end 22, and apart from the differences described below, the operation of system 126 is generally similar to that of system 26 (FIGS. 1-4), so that elements indicated by the same reference numerals in both systems 26 and 126 are generally similar in construction and in operation.

Figure 10:
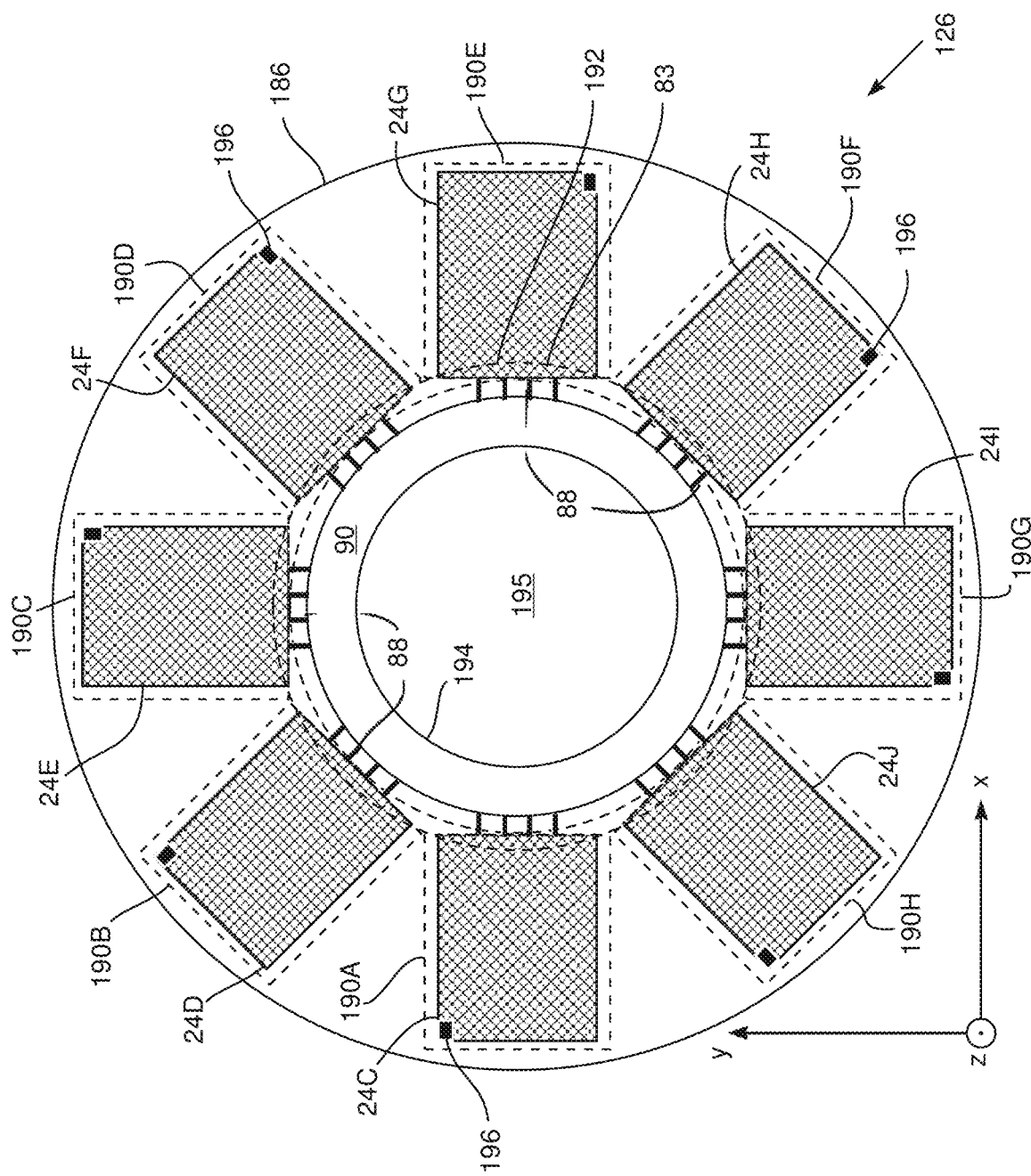
FIG. 10 and FIG. 11 illustrate the imaging array system of FIGS. 8 and 9 in its unfolded state, according to the further alternative embodiment of the present invention.
Figure 11:
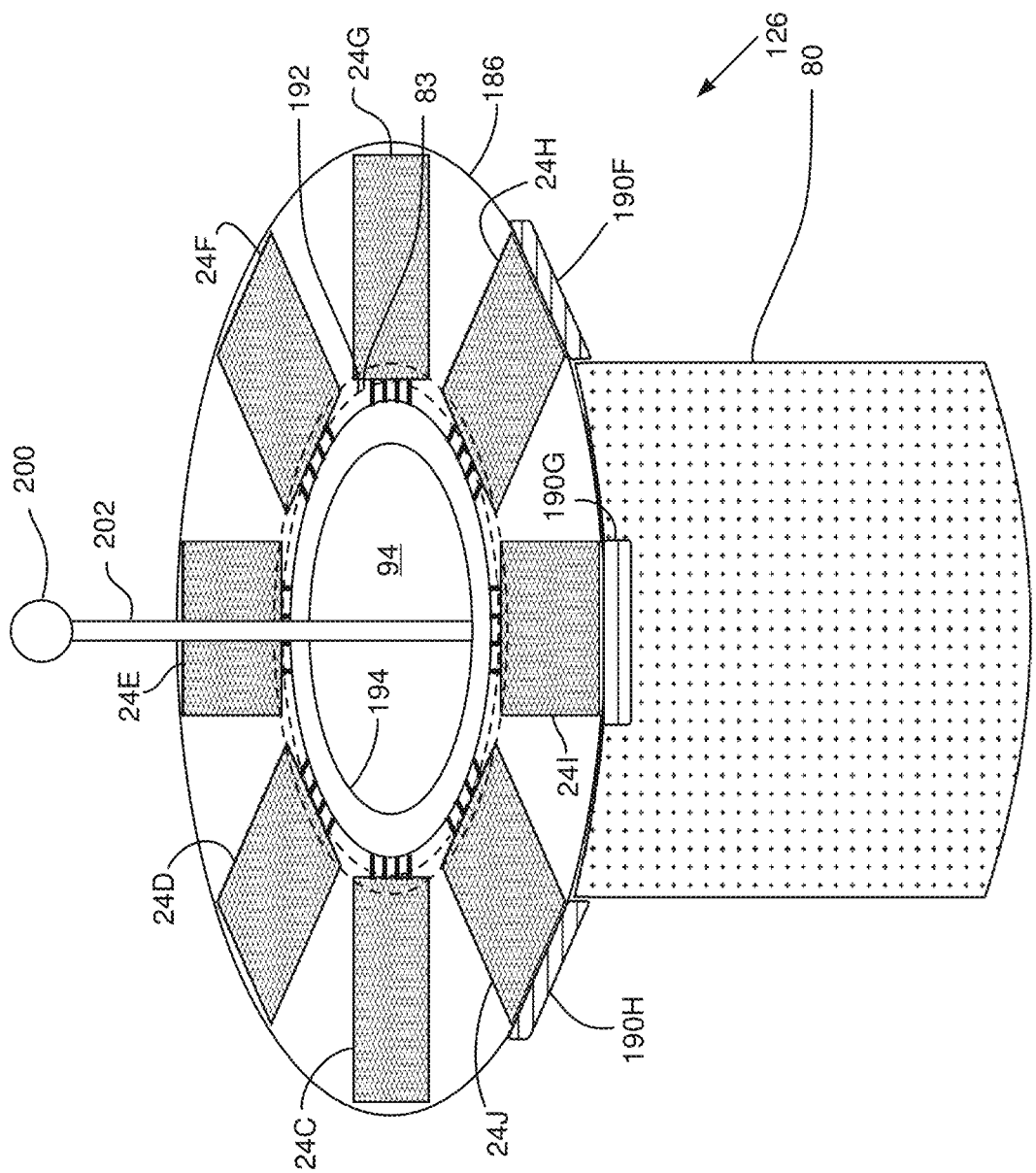

FIG. 8 illustrates the probe distal end as it is being looked into, and shows probe distal end 22 as comprising external insertion tube 80 enclosing catheter lumen 90 having a lumen diameter, as described above with regard to FIG. 2. FIG. 9 is a schematic cross-section of FIG. 8, taken along a line IX-IX. FIGS. 8 and 9 illustrate imaging array system 126, described in more detail below, in its folded state, and FIGS. 10 and 11 illustrate the imaging system in its unfolded state. For clarity, FIGS. 8, 9, and 10 have been drawn on a set of xyz orthogonal axes.

For array system 126, a tubular channel 194, having a diameter smaller than the lumen diameter of lumen 90, is positioned in lumen 90, the tubular channel enclosing a channel lumen 195. As is illustrated in FIG. 8, system 126 in its folded state fits into a portion of lumen 90 lying between inner wall 79 of tube 80 and an outer wall 193 of channel 194.

System 126 comprises eight generally similar planar 2D arrays 24C, 24D, 24E, 24F, 24G, 24H, 24I, 24J mounted symmetrically on a flexible circuit substrate 186, typically a flexible printed circuit substrate. Arrays 24C, 24D, . . . 24I, 24J have transverse dimensions that are less than the diameter of lumen 90. While the transverse dimensions of arrays 24C, 24D, . . . 24I, 24J may be different from those of arrays 24A, 24B, references above to arrays 24 also apply, mutatis mutandis, to arrays 24C, 24D, . . . 24I, 24J. Flexible printed circuit substrate 186 is mounted on and is supported by a support structure 185, which has a structure distal end 182 that is foldable, substantially as described herein for structure 85. Typically, a proximal end of structure 185 does not fold.

Structure 185 has a generally cylindrical shape, but at structure distal end 182, the cylindrical shape separates into eight generally similar rectangular "fingers" 190A, 190B, 190C, . . . 190F, 190G, 190H, herein also referred to as fingers 190AH. Fingers 190AH are connected to the proximal end of structure 185, and fold about a circular hinge line 192 in the structure. It will be understood that the proximal end of structure 185 completely surrounds channel 194, i.e., any ray projected outward from channel 194 intersects structure 185.

FIGS. 8 and 9 illustrate imaging array system 126 in its folded state, in which state both the distal and the proximal ends of the array system are able to fit completely within insertion tube 80, i.e. into lumen 90, in the space between channel 194 and tube 80. For clarity, the schematic cross-section of FIG. 9 does not include channel 194, so that flexible circuit substrate 186 is visible. As for system 26, in system 126 electrical interconnects 88 from each of the arrays of system 126 are formed on substrate 186, typically by lithographing conductive traces onto the substrate.

FIGS. 10 and 11 illustrate imaging array system 126 in its unfolded state, in which state the proximal ends of support structure 185 and substrate 186 are able to fit completely within insertion tube 80, i.e. into lumen 90, in the space between channel 194 and tube 80.

In the unfolded state circular hinge line 192 approximately coincides with circular opening 83, and fingers 190AH are folded by 90° from the z-axis, around hinge line 192. In contrast to system 26, to accomplish the unfolding fingers 190AH do not rotate in countervailing directions, but rather rotate in a common direction about hinge line 192. Similarly, to return to a folded state, fingers 190AH rotate in a common direction, opposite to that for the unfolding, about line 192.

As illustrated in FIG. 10, in the unfolded state fingers 190AH splay outwards and unfold substrate 186 from its generally cylindrical shape (shown in cross-section in FIG. 8), into a 2D disc, so that arrays 24C, 24D, . . . 24I, 24J, which are attached to the substrate, lie in an xy plane, and are symmetrically disposed about a center of insertion tube 80. In the unfolded state arrays 24C, 24D, . . . 24I, 24J form a large imaging array having a diameter, typically between 6 mm and 10 mm, that is two or more times larger than the diameter of insertion tube 80.

It will be understood that since lumen 195 is open, intervention devices and/or fluids such as irrigation fluid may be inserted through the lumen. Furthermore, the intervention devices and/or fluids can be inserted through lumen 195 without interfering with the operation of array system 126.

In some embodiments respective tracking sensors 196, generally similar in function to sensor 52, are fixed to arrays 24C, 24D, . . . 24I, 24J, the sensors enabling processor 46 to determine the location and orientation of each of the arrays. Using this calibration information, the processor is able to correct in real time for imperfect deployment or deformation of the arrays, due, for example, to applied forces between the arrays or by blood or saline flowing around the arrays. The corrections typically include changing beamforming time delays in transmit and receive beamforming operations, so that the data generated is correctly delayed and added to achieve an optimum signal-to-noise level and an optimum point spread function of a volumetric image generated by the separate arrays.

Alternatively, each array 24C, 24D, . . . 24I, 24J may be used as an independent imaging array acquiring a separate image. In some embodiments the separate images may be stitched together to form a larger image.

Further alternatively, typically when imaging array system 126 in its unfolded state has dimensions which are repeatable, the locations and orientations of arrays 24C, 24D, . . . 24I, 24J, relative to each other, i.e., the calibration information for the array system, may be determined by using the unfolded system to image a known target in a water bath. Once the array relative locations and orientations have been measured, the array system 126 is calibrated and may be used for the procedures referred to above, and the time delay corrections described above may be implemented. In this case it will be appreciated that sensors 196 may not be necessary.

FIG. 11 is a perspective view of system 126 in its unfolded state. The figure illustrates a yet further method for calibrating the locations and orientations of arrays 24C, 24D, . . . 24I, 24J, relative to each other. An ultrasound beacon 200, typically an ultrasound generator, is positioned at a known location relative to insertion tube 80. Beacon 200 acts as an active ultrasound target. Typically beacon 200 is attached to a rod 202, the position of which is controlled by professional 14. Using rod 202, the professional may move beacon 200 along a symmetry axis of insertion tube 80, at a preset distance above edge 83. Processor then acquires images from arrays 24C, 24D, . . . 24I, 24J, and uses the image of beacon 200 in the acquired images to register and calibrate the arrays.

The calibration process illustrated in FIG. 11 may be implemented once unfolded system array 126 is at a desired target position, such as within a chamber of the heart. Alternatively, rather than beacon 200 being an active ultrasound generator, beacon 200 may comprise a passive target. Further alternatively, registration and calibration of arrays 24C, 24D, . . . 24I, 24J, may be accomplished using images of the target that are acquired simultaneously.

FIGS. 12, 13, 14, and 15 are schematic illustrations of distal end 22 of probe 20, according to a yet further alternative embodiment of the present invention.

An imaging array system 226 is incorporated into probe distal end 22, and apart from the differences described below, the operation of system 226 is generally similar to that of system 126 (FIGS. 8-11). Elements indicated by the same reference numerals in both systems 126 and 226, are generally similar in construction and in operation, and the descriptions for FIGS. 8, 9, 10, and 11 respectively apply, mutatis mutandis, to FIGS. 12, 13, 14, and 15. In addition, operations such as the calibration processes described above for array 126 are generally the same, mutatis mutandis, for array 226.

Figure 14:
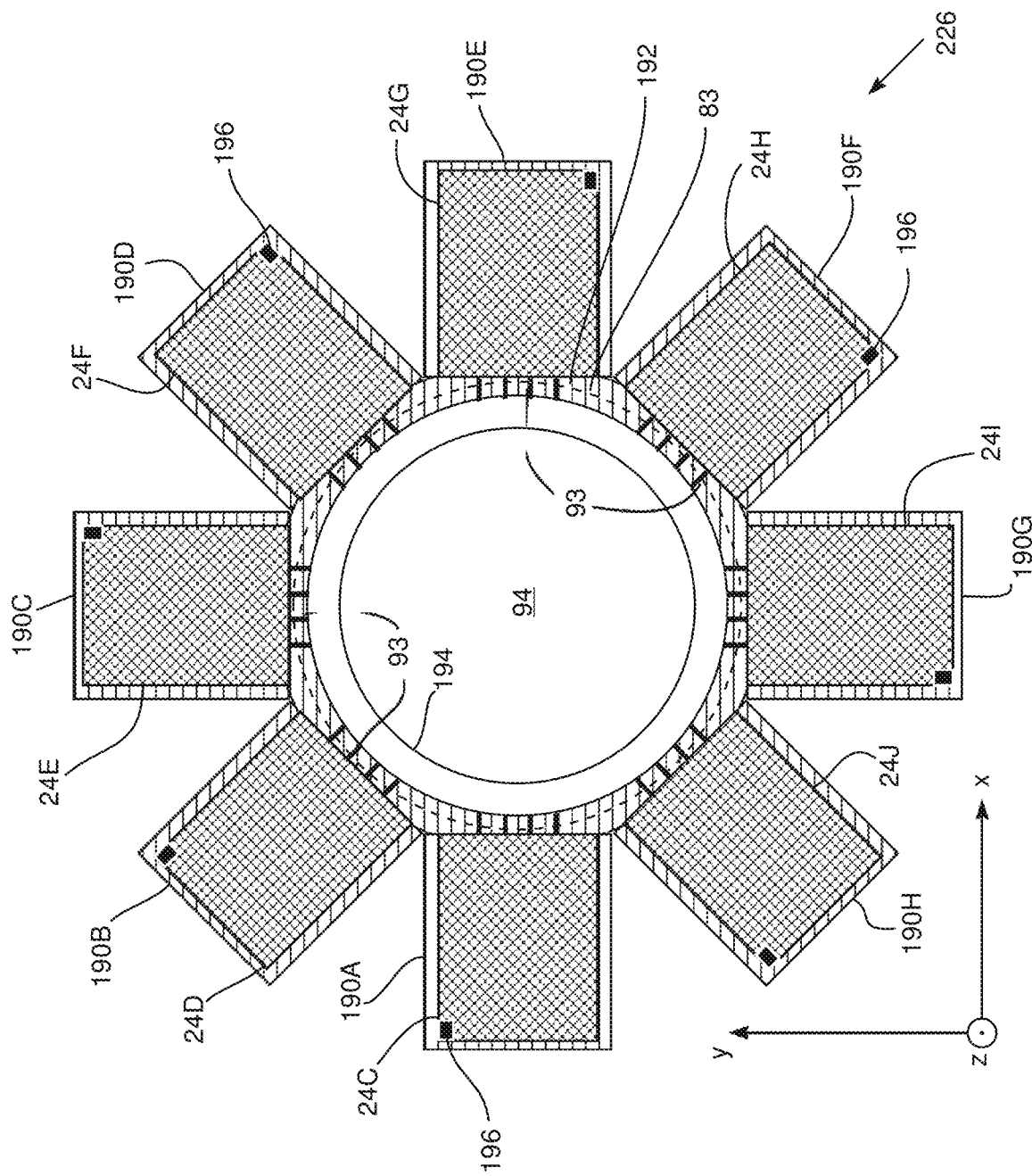
Figure 15:
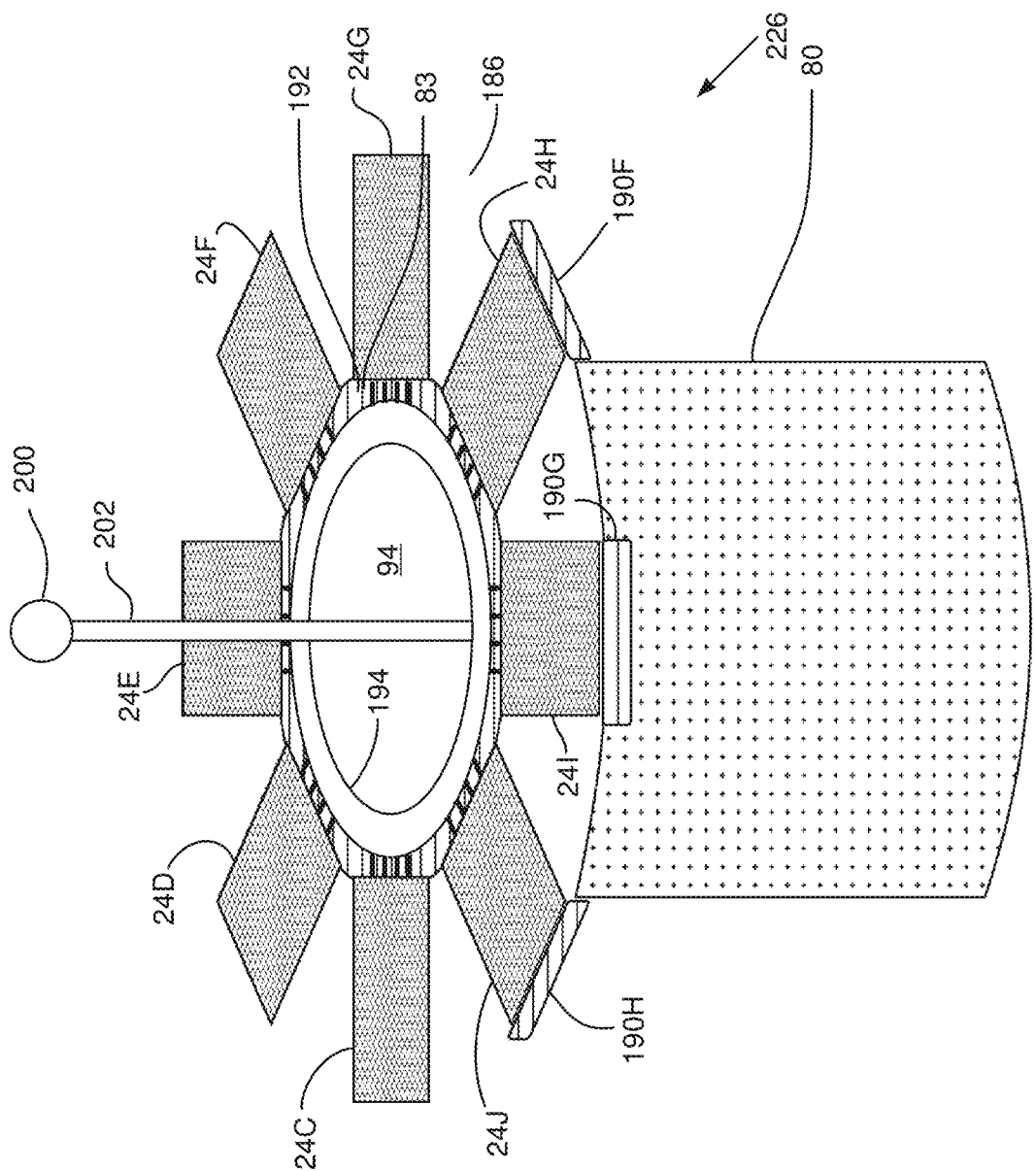

FIG. 12 illustrates the probe distal end as it is being looked into, and shows probe distal end 22 as comprising external insertion tube 80 enclosing catheter lumen 90 having a lumen diameter, as described above with regard to FIG. 2. FIG. 13 is a schematic cross-section of FIG. 12, taken along a line XIII-XIII. FIGS. 12 and 13 illustrate imaging array system 226, described in more detail below, in its folded state, and FIGS. 14 and 15 illustrate the imaging system in its unfolded state. For clarity, FIGS. 12, 13, and 14 have been drawn on a set of xyz orthogonal axes.

As for array system 126, in array 226 tubular channel 194, having a diameter smaller than the lumen diameter of lumen 90, is positioned in lumen 90, the tubular channel enclosing a channel lumen 195. As is illustrated in FIG. 12, system 226 in its folded state fits into a portion of lumen 90 lying between inner wall 79 of tube 80 and an outer wall 193 of channel 194.

In contrast to system 126, system 226 does not use a flexible substrate 186. Rather, arrays 24C, 24D, . . . 24I, 24J are respectively directly mounted on rectangular fingers 190A, 190B, 190C, . . . 190F, 190G, 190H of support structure 185. In addition, since there is no flexible substrate, electrical interconnects to the arrays are formed as conductive wires 93 that connect directly to the arrays.

FIGS. 12 and 13 illustrate imaging array system 226 in its folded state, in which state both the distal and the proximal ends of the array system and its support structure are able to fit completely within insertion tube 80, i.e. into lumen 90, in the space between channel 194 and tube 80, and also completely surround channel 194. For clarity, the schematic cross-section of FIG. 13 does not include channel 194, so that structure 185 is visible.

FIGS. 14 and 15 illustrate imaging array system 226 in its unfolded state, in which state the proximal end of support structure 185 is able to fit completely within insertion tube 80, i.e. into lumen 90, in the space between channel 194 and tube 80, and also completely surround channel 194.

The description above describes embodiments having two and eight 2D arrays which fold into a lumen and which unfold out of the lumen to form an array having a transverse dimension greater than that of the lumen. However, embodiments of the present invention comprise other numbers of 2D arrays which fold into a lumen, and which unfold out of the lumen to form an array having a transverse dimension greater than that of the lumen.

As examples, rather than having two arrays connected as a letter V, as described with reference to FIGS. 1-4, one embodiment has three arrays connected as a letter N, a second embodiment has four arrays connected as a letter M, and in general any number of arrays may be connected and hinged together in a concertina manner. In addition, rather than having eight arrays distributed symmetrically and mounted on a substrate, as described with reference to FIGS. 5-8, any number of two or more arrays may be mounted on the substrate, and be supported by respective supports, and the two or more arrays may be distributed symmetrically or unsymmetrically on the substrate.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:

an insertion tube, configured to be inserted into a body cavity and having a first lumen therethrough having a first lumen diameter and a distal opening;

a tubular channel, having a second lumen therethrough and an outer channel diameter smaller than the first lumen diameter, inserted into the first lumen; and a support structure, which is configured to be passed through a space between an inner wall of the insertion tube and an outer wall of the tubular channel to the distal opening in a folded state and to unfold, upon exit of the support structure through the distal opening, in a direction transverse to the first lumen to reach a dimension that is greater than the first lumen diameter, a plurality of planar two-dimensional (2D) arrays of ultrasonic transducers supported by the support structure, the arrays having transverse dimensions less than the first lumen diameter, wherein the support structure comprises two 2D supports connected by a hinge which has a rotation axis parallel to a central symmetry axis of the first lumen, the two 2D supports and the hinge formed of a single piece of material at, at least, a distal end, the hinge being a common element disposed between the two 2D supports so that the single piece of material is foldable about a support hinge line, the two 2D supports fold about the hinge in countervailing directions to place the support structure in an unfolded state, the plurality of planar 2D arrays comprises two 2D arrays respectively mounted on the two 2D supports, wherein in an unfolded state of the support structure, the plurality of 2D arrays lie in a single plane, wherein a normal of the single plane is orthogonal to a symmetry axis of the first lumen, and wherein the 2D arrays are disposed on a flexible substrate, the flexible substrate disposed on the single piece of material and being foldable along a substrate hinge line parallel to and above the support hinge line, to define a gap between the flexible substrate and the single piece of material, the gap disposed between the substrate hinge line and the support hinge line.

2. The apparatus according to claim 1, wherein the flexible substrate spans the gap.

3. A method, comprising:
inserting an insertion tube into a body cavity, the tube having a first lumen therethrough having a first lumen diameter and a distal opening;
inserting a tubular channel, having a second lumen therethrough and an outer channel diameter smaller than the first lumen diameter, into the first lumen;
passing a support structure through a space between an inner wall of the insertion tube and an outer wall of the tubular channel to the distal opening in a folded state; and
unfolding the support structure, upon exit of the support structure through the distal opening, in a direction transverse to the first lumen to reach a support dimension that is greater than the first lumen diameter,
supporting a plurality of planar two-dimensional (2D) arrays of ultrasonic transducers by the support structure, the arrays having transverse dimensions less than the first lumen diameter,
wherein the support structure comprises two 2D supports connected by a hinge which has a rotation axis parallel to a central symmetry axis of the first lumen, the two 2D supports and the hinge formed of a single piece of material at, at least, a distal end, the hinge being a common element disposed between the two 2D supports so that the single piece of material is foldable about a support hinge line,
the two 2D supports fold about the hinge in countervailing directions to place the support structure in an unfolded state,
the plurality of planar 2D arrays comprises two 2D arrays respectively mounted on the two 2D supports,
wherein in an unfolded state of the support structure, the plurality of 2D arrays lie in a single plane,
wherein a normal of the single plane is orthogonal to a symmetry axis of the first lumen, and
wherein the 2D arrays are disposed on a flexible substrate, the flexible substrate disposed on the single piece of material and being foldable along a substrate hinge line parallel to and above the support hinge line, to define a gap between the flexible substrate and the single piece of material, the gap disposed between the substrate hinge line and the support hinge line.

4. The method according to claim 3, wherein the flexible substrate spans the gap.

* * * * *